United States Patent [19]

Schendel et al.

[11] Patent Number: 5,030,563
[45] Date of Patent: Jul. 9, 1991

[54] BACTERIAL HYPERSECRETION USING MUTANT REPRESSOR SEQUENCE

[75] Inventors: Paul F. Schendel, Wayland, Mass.; Marc Nasoff, San Diego, Calif.; Patricia Raney, Somerville, Mass.

[73] Assignee: Genetics Institute, Inc., Cambridge, Mass.

[21] Appl. No.: 476,097

[22] Filed: Jan. 26, 1990

Related U.S. Application Data

[63] Continuation of Ser. No. 71,458, Jul. 7, 1987, abandoned.

[51] Int. Cl.$^5$ .................. C12P 21/00; C12N 1/20; C12N 15/00
[52] U.S. Cl. ............... 435/698; 435/691; 435/172.3; 435/252.3; 435/252.33; 435/320.1; 435/91; 536/27; 935/11; 935/23; 935/29; 935/39; 935/41; 935/72; 935/73
[58] Field of Search ............ 435/91, 172.1, 172.3, 435/320, 252.33, 69.1, 69.8; 935/11, 23, 29, 39, 41, 72, 73

[56] References Cited

FOREIGN PATENT DOCUMENTS 0131843 1/1985 European Pat. Off. .
WO 87/03300 6/1987 PCT Int'l Appl. .

OTHER PUBLICATIONS

Lambert et al., (1985), *J. Bact.*, vol. 162, pp. 441–444.
Windle et al., (1986), vol. 95, pp. 95–99, *Acne.*
Hoffman et al., *Pac Natl. Acad. Sci.,* vol. 82, p. 5107, 1985.
Ernst et al., *Chem. Abst.,* vol. 107 (15), No. 128972a, "DNA Sequence, Multicopy Expression Vector, and Transformed Host for Enhanced Secretion of Heterologous Proteins Using Substituted Promoters".
Spicer et al., *J. Biol. Chem.,* 050294321 257(10): 5716 (1982).

Primary Examiner—Robin L. Teskin
Attorney, Agent, or Firm—Luann Cserr; Bruce Eisen

[57] ABSTRACT

An improved bacterial host cell useful for the inducible production and secretion in high yields of a heterologous protein is provided which contains a gene encoding the heterologous protein operatively linked to a secretory leader-encoding sequence and to an expression control sequence which contains a promoter region; and a second DNA sequence encoding a repressor capable of binding to said promoter region. The cell contains at least a mutation in the repressor binding region of the promoter or a mutation in the promoter binding region of the repressor-encoding sequence; or mutations in both regions. These mutation(s) lower the frequency of transcriptional induction by the promoter from the observed with the wild-type promoter and/or repressor-encoding sequence, resulting in higher yields of secreted heterologous protein.

6 Claims, 3 Drawing Sheets

Figure 1

```
                                        312
ATG AGC ACA AAA AAG AAA CCA TTA ACA CAA GAG CAG CTT GAG GAC
        339                                 366
GCA CGT CGC CCT AAA GCA ATT TAT GAA AAA AAG AAA AAT GAA CTT
                    393                                 420
GGC TTA TCC CAG GAA TCT GTC GCA GAC AAG ATG GGG ATG GGG CAG
                                447
TCA GGC GTT AGT GCT TTA TTT AAT GGC ATC AAT GCA TTA AAT GCT
            474                                 501
TAT AAC GCC GCA TTG CTT ACA AAA ATT CTC AAA GTT AGC GTT GAA
                        528                                 555
GAA TTT AGC CCT TCA ATC GCC AGA GAA ATC TAC GAG ATG TAT GAA
                                582
GCG GTT AGT ATG CAG CCG TCA CTT AGA AGT GAG TAT GAG TAC CCT
        609                                 636
GTT TTT TCT CAT GTT CAG GCA GGG ATG TTC TCA CCT AAG CTT AGA
                    663                                 690
ACC TTT ACC AAA GGT GAT GCG GAG AGA TGG GTA AGC ACA ACC AAA
                            717
AAA GCC AGT GAT TCT GCA TTC TGG CTT GAG GTT GAA GGT AAT TCC
        744                                 771
ATG ACC GCA CCA ACA GGC TCC AAG CCA AGC TTT CCT GAC GGA ATG
                    798                                 825
TTA ATT CTC GTT GAC CCT GAG CAG GCT GTT GAG CCA GGT GAT TTC
                                852
TGC ATA GCC AGA CTT GGG GGT GAT GAG TTT ACC TTC AAG AAA CTG
            879                                 906
ATC AGG GAT AGC GGT CAG GTG TTT TTA CAA CCA CTA AAC CCA CAG
                        933                                 960
TAC CCA ATG ATC CCA TGC AAT GAG AGT TGT TCC GTT GTG GGG AAA
                                987
GTT ATC GCT AGT CAG TGG CCT GAA GAG ACG TTT GGC TGA
```

Figure 2

A) Wild-Type pL Promoter:

GGCGGTGTTGACATAAATACCACTGGCGGTGATACTGAGCACAT

B) Mutant pL Promoter:

GGCGGTGTTGACATAAATACCACTGGCGGTGATACCGAGCACAT

Figure 3

(5') AAAAATATAACTTTCATTTTTTTTATTTTATTAGCATCGCCATTATATGCG (3')

(3') TTTTTATATTGAAAGTAAAAAAAATAAAATAATCGTAGCGGTAATATACGC (5')

BACTERIAL HYPERSECRETION USING MUTANT REPRESSOR SEQUENCE

This application is a continuation, of U.S. application Ser. No. 071,458, filed 7/7/87 now abandoned.

The present invention relates to the secretion of heterologous proteins into the periplasmic space of gram-negative bacteria or into the media from gram-positive bacteria. More specifically, it concerns bacterial host cells and methods for engineering and isolating bacterial strains which are capable of secreting high levels of heterologous proteins in an active form.

BACKGROUND OF THE INVENTION

One of the primary mechanisms of gene regulation in prokaryotes involves the interaction between specific DNA sequences, called operators, and regulatory proteins, called repressors. In general a repressor will interact with only one operator, or a small set of operators. This binding interaction is very tight and specific for the operator sequence. When repressor is bound to the operator site, it prevents the interaction of RNA polymerase with its promoter site, a sequence of DNA which overlaps the operator and is the site at which RNA polymerase binds to initiate transcription.

Several prokaryotic regulatory systems have been studied in detail. These include the *E. coli* lac and trp operon regulatory systems, and the bacteriophage lambda major leftward and rightward promoters, pL and pR. [See, e.g., Beckwith, J., *Escherichia coli and Salmonella typhimurium, Cellular and Molecular Biology*, (F. Neidhardt, ed.) ASM Press, Washington, D.C., p1444-1452 (1987); Yanofsky, C. and Crawford, I., *Escherichia coli and Salmonella typhimurium, Cellular and Molecular Biology*, (F. Neidhardt, ed.) ASM Press, Washington, D.C., p1453-1472 (1987); and Gussin, G., et al., Lambda II (Hendrix, Roberts, Stahl, and Weisberg, eds) Cold Spring Harbor Laboratory Press, Cold Spring Harbor, N.Y., p93-121 (1983)]. Moreover these systems have been used to develop controllable expression vectors for the intracellular production of heterologous proteins [See, e.g., Remaut et al, *Gene*, 15:81 (1981); Rosenberg et al, *Meth. Enzymol.*, 101:123 (1983); Backman and Ptashne (1978) *Cell*, 13:65 (1978); Edman et al, *Nature*, 291:503 (1981)]. All of these expression systems have focussed on using strong promoters so that transcription is maximal and expression rates are high.

Attempts have also been made to develop systems which will secrete heterologous proteins from bacterial cells. [See, e.g., U.S. Pat. No. 4,411,994; Masui et al, *Bio/Technology*, 81-85 (January 1984); and Emerick et al, *Bio/Technology*, 165-168 (February 1984)]. These systems have generally given disappointingly low yields of the desired protein. Once again relatively strong promoters have generally been employed to generate the message encoding the protein to be secreted.

BRIEF SUMMARY OF THE INVENTION

In contrast to prior art approaches aimed at increasing the production rate and/or level of heterologous proteins by maximizing transcription rates, e.g. with strong promoters, we have surprisingly discovered that novel bacterial host strains capable of secreting biologically active heterologous proteins at a considerably higher level than wild-type strains can be produced by decreasing the rate of synthesis of the heterologous protein. One method in particular for doing so involves decreasing the transcription rate for the gene to be expressed. In order to so decrease the rate of transcription, or perhaps more precisely, to decrease the rate of induction of transcription, we mutagenize the promoter nucleotide sequence and/or the repressor gene sequence to alter either the strength of the promoter or the interaction between repressor and operator. The likely proximal effect of this selective mutagenesis is to slow the transcription rate, or the rate of induction of transcription, for the heterologous gene. Regardless of the precise mechanism, the mutagenesis achieves a balance between transcription, translation and secretion rates to enhance secretion of active protein.

Thus the invention in one aspect involves an improved bacterial host cell, useful for the inducible production of a heterologous protein. The host cell contains a gene encoding the heterologous protein operatively linked to a secretory leader-encoding sequence, and to an expression control sequence which contains a promoter region; and a second DNA sequence encoding a repressor capable of binding to the promoter region. The improved host cell is characterized by containing at least one of the following mutations:

(a) a mutation present in the repressor binding region of the promoter:

(b) a mutation present in the promoter binding region of the repressor-encoding sequence; or (c) a mutation present in the repressor binding region of the promoter and a mutation present in the promoter binding region of the repressor-encoding gene.

The functional limitation on the specific mutations employed is that they lower the frequency of transcriptional induction by the promoter from that observed with the wild-type promoter and/or repressor-encoding sequence, resulting in higher yields of secreted heterologous protein.

This invention further contemplates the use of any mutation within the heterologous DNA sequence which affects the rate of translation. For example, a mutation at the region corresponding to the ribosome binding site on the mRNA corresponding to the heterologous DNA sequence may slow translation and thus protein synthesis in the cell. In that aspect of the invention the mutation results in a decreased rate of protein synthesis by virtue of decreasing the rate of protein translation. Such mutations may be produced and identified by the mutagenesis and screening methods disclosed hereinafter in the examples involving mutations in transcriptional regulatory elements (promoter/repressor). Similarly mutations in host cell translational initiation or elongation factors, or the use of low copy number plasmids may effect such a decrease in the rate of translation.

Conventional mutagenesis techniques may be employed on presently available promoter/repressor gene pairs to develop the novel host cells embodying the transcriptional modifications described herein. Similarly, one can employ known mutant promoters or repressors in the host cell described above. The optimal transcription/secretion balance of the selected cell in which the mutant elements are incorporated can be determined through simply comparing, by any conventional assay for the selected heterologous protein, expression from a wild-type repressor/operator/promoter system with that of the novel mutagenized system.

One embodiment of the product of such a method is an improved bacterial host cell. The host cell may be *E. coli* or other enteric bacteria, various bacilli or other known bacterial strains. Both gram-negative and gram-positive bacterial strains may be employed as host cells according to the invention. An improved host cell of the invention may contain a wild-type pL promoter and a mutant $C_I$ repressor gene. Alternatively, it may contain a mutant promoter with a normal (wild-type) repressor. In another embodiment, an improved host cell may contain both a mutant promoter and a mutant repressor. These same combinations may be repeated for the pR promoter and the $C_I$ repressor, the lac promoter and its repressor, the trp promoter and its repressor, or any other bacterial or phage promoter/operator/repressor system.

One presently preferred improved bacterial host cell for the production and secretion of a heterologous protein in high yield includes in it a DNA sequence comprising a gene encoding a heterologous protein operatively linked to a secretory leaderencoded sequence and to an expression control sequence which contains a pL or pR promoter region; and a second DNA sequence encoding the Ser-48 $C_I$857 repressor, the same or substantially the same as depicted in FIG. 1.

Another preferred embodiment is a bacterial host cell containing a DNA sequence comprising a gene encoding the heterologous protein operatively linked to a secretory leader-encoding sequence and to an expression control sequence which contains a mutagenized pL promoter region the same or substantially the same as depicted in FIG. 2B; and a DNA sequence encoding a $C_I$857 repressor.

Secretory leader sequences are also a component of the improved cells of the present invention. Conventional sequences are well known to those of skill in the art and may be employed in the construction of these improved host cells. One desirable secretory leader-encoding sequence for use in the novel bacterial host cells of the present invention includes a synthetically DNA sequence the same or substantially the same as depicted in FIG. 3.

Another aspect of the invention is a method for secreting active heterologous protein in high yield from bacterial host cells which involves culturing an improved bacterial host cell according to the invention under conventional conditions permitting the production and secretion of the heterologous protein. Many heterologous proteins may be produced in the novel host cells generated by the methods of the present invention. Of particular interest are lymphokines, cytokines, growth factors, other hormones and enzymes.

Other aspects and advantages of the present invention will be apparent upon consideration of the following detailed description of the invention, including illustrative examples of the practice thereof.

BRIEF DESCRIPTION OF THE FIGURES

FIG. 1 is the sequence of the $C_I$857 Ser-48 allele of the lambda CI gene.

FIG. 2 illustrates the wild-type and mutant sequences of the pL promoter.

FIG. 3 illustrates an exemplary synthetic secretion leader encoding sequence from the heat labile enterotoxin gene.

DETAILED DESCRIPTION OF THE INVENTION

The present invention involves improved bacterial host cells which contain mutant promoters and/or mutant repressors which reduce, rather than enhance, the transcriptional efficiency of the expression system. This reduction in rate of transcription allows the secretory mechanisms in the cell to process the heterologous protein while it is still soluble inside the cell, and thus maximize the amount of protein secreted in active form.

The functional limitation on the type of mutant promoter or mutant repressor gene in the improved host cell is that the mutant promoter/repressor system must permit at least some reduction in the rate of transcription or transcriptional induction of the heterologous gene. Neither a completely destroyed or inoperable promoter nor a repressor mutant that cannot release from the operator to allow at least some transcription is useful in the improved host cell of the invention.

In some cases, the high level expression of a heterologous protein in a host cell is lethal. The lethality may reflect the inability of the secretion apparatus of the cell to process proteins produced at such a great rate, regardless of the presence of secretory leader peptides. The selection of mutants that can survive under conditions where such expression is lethal in wild type can lead to the selection of a mutant repressor/promoter pair with reduced expression rate. Mutants with increased secretion rate can then be identified from among these survivors.

In order to identify mutants which not only survive but have enhanced rates of secretion, a secretion screen is employed, e.g. according to techniques described by Hoffman and Wright, *Proc. Natl. Acad. Sci. USA*, 82:5107 (1985). The secretion screen allows analysis of individual colonies on a plate for the secretion of an assayable enzyme activity, where the assayable enzyme is fused to the heterologous protein of interest. If such a screening technique is used, more random mutagenesis techniques can be used to generate the desired mutant repressor/promoter pairs. In these cases, the entire promoter region or the DNA binding domain of the repressor can be randomly altered by conventional chemical mutagenesis techniques and mutants characterized by improved secretion levels may be conveniently selected. An appropriate mutant pair providing reduced transcription of the heterologous gene can be identified by such methods of secretion screening.

To develop a novel bacterial host cell according to the invention, a mutant promoter or mutant repressor sequence may be selected and then incorporated into a plasmid with other conventional elements. The starting mutant promoter/repressor pair to serve as the substrate for the mutagenesis may be selected from among such mutants presently available and described in the art. Studies of the binding of mutant repressors to their operators [See, e.g, Nelson and Sauer, *Cell*, 42:549 (1985); Nelson and Sauer, *J. Mol. Biol.* 192:27 (1986); and Gussin, et al., *Lambda II,* (Hendrix, Roberts, Stahl, and Weisberg, eds) Cold Spring Harbor Press, Cold Spring Harbor, N.Y., p. 93-123 (1983)] permit the selection of known mutant promoter and/or mutant repressor sequences which may provide reduced, but not abolished, transcriptional rates. This selected promoter region is incorporated into a heterologous expression plasmid and then altered by conventional site-directed mutagenesis [see, e.g., Morinaga, et al., *Biotechnology,*

2:636 (1984)]. Alternatively, the repressor-encoding sequence is altered in an analogous fashion. The resultant mutant repressor/promoter pair is analyzed for its ability to promote secretion of the heterologous protein by comparison of expression with the wild-type plasmid not having been subjected to the site-directed mutagenesis.

The following examples illustrate specific embodiments of the methods and products of the invention. In experiments using four different heterologous genes and modified $C_I$ repressors or pL promoters, we have observed significantly improved yields over the yields obtained with wild-type expression systems. It is contemplated that this method will be of general applicability to other strains of *E. coli* and to other microbial species and to other promoter/repressor pairs. It is also contemplated that this invention will not be limited by the choice of heterologous protein to be produced, and in fact will be broadly applicable to the production in secreted form of any desired protein.

EXAMPLE I

Preparation of a Bacterial Host with a Mutant pL Promoter

The lambda pL promotor sequence, illustrated in FIG. 2A, consists of an overlapping near consensus promoter and parts of the ORI and ORII operator sequences. A mutation was made in the −10 region of the promoter by standard methods to generate the sequence of FIG. 2B. This mutant promoter still binds lambda repressor efficiently, but has a substantially weaker transcription promoting capacity as compared with the wild-type pL promoter.

A plasmid containing a colE1 origin of replication was constructed according to standard techniques containing the above-mentioned mutant promoter sequence operatively linked to the sequence of FIG. 3, which encodes a secretory leader sequence. This sequence was in turn fused to the coding sequence for the selected hererologous gene, GM-CSF described by Wong, et al., *Science*, 228:810 (1985) which was in turn fused to the alkaline phosphatase phoA gene of E. coli. Such a plasmid thus contains in 5'→3' order, the mutagenized pL promoter, leaderencoding sequence, GM-CSF-encoding cDNA (or a cDNA encoding any desired protein) and phoA gene. *E. coli* cells which contain and are capable of expressing the $C_I$ repressor are then transformed with the plasmid using purely conventional techniques. When transcription of the heterologous gene is induced (using standard induction conditions), a protein is produced which has the secretory leader sequence at its N-terminal end, fused to GM-CSF in the middle, fused to alkaline phosphatase at its C-terminal end. When secreted, this protein has alkaline phosphatase activity and can be assayed by conven-tional means [See, e.g., Miller, J., *Experiments in Molecular Genetics*, Cold Spring Harbor Press, Cold Spring Harbor, N.Y. (1972)]. This is a particularly appropriate model system since the phoA gene product has alkaline phosphatase activity only after secretion from the transformed host cells. The ability of the mutant and wild type promoter sequences to effect secretion of this fusion protein were measured. The mutant produced far less total protein but surprisingly yielded significantly more secreted alkaline phosphatase activity in the cell's periplasm relative to the corresponding experiment performed with the wild type pL promoter.

EXAMPLE II

Preparation of a Bacterial Host with a Mutant Lambda $C_I$ Repressor Gene

The $C_I$, rex and N region of bacteriophage lambda contained in nucleotides 34499 to 38214, as described by F. Sanger et al. *J. Mol. Biol.*, 162:729 (1982) were inserted into the ClaI site of the lacZ gene which had been cloned onto a plasmid using purely conventional methods and materials. The $C_I$ gene used was the 857 allele. The sequence of this gene was then altered by conventional methods so that the glycine-48 codon was changed to a serine codon. (G to A transition in first position.) This Ser-48 $C_I$ 857 allele was then inserted into the *E. coli* genome via conventional homologous recombination into the lacZ gene of the cell. Once inserted it yielded a lacZ, lambda immune *E. coli*. Plasmids carrying the wild-type pL promoter sequence operatively linked to the secretory leader, GM-CSF, phoA fusion gene described in Example I were introduced into this host by conventional transformation. The amount of alkaline phosphatase activity produced (i.e., upon secretion from the transformants) when synthesis was induced at high temperature was significantly greater than produced in control experiments using the same plasmid in a host cell containing the gly-48 $C_I$857.

EXAMPLE III

Expression and Secretion of Heterologous Genes

A. The gene for GM-CSF, as described by Wong et al, supra or human IL-6, as described in pending U.S. patent application Ser. No. 47,957 which is incorporated herein by reference, was fused to the sequence encoding the secretory leader sequence as in Example II, but without the phoA sequence. These sequences were operatively linked to the wild-type pL promoter sequence on a conventional *E. coli*-compatible plasmid and transformed into *E. coli* cells carrying either Ser-48 $C_{I857}$ or Gly-48 $C_I$857. In both cases, the cells with the Ser-48 $C_{I857}$ gene produced significantly more of the desired protein in the periplasm as did the corresponding transformant cells containing the Gly-48 $C_I$857.

B. A gene fusion entirely analogous to the one described in Example II but containing a modified human proinsulin gene sequence (as described in International patent application PCT/US85/01673) in place of the GM-CSF sequence was prepared. When transfected into cells carrying either Ser-48 $C_I$857 or Gly-48 $C_I$857, significantly more alkaline phosphatase activity was detected in the Ser-48 $C_I$857 containing cell than in cells with Gly-48 $C_I$857, indicating much higher rates of secretion of the proinsulin/alkaline phosphatase fusion protein in the cells with an altered repressor protein (Ser-48 $C_I$857).

Numerous modifications may be made by one skilled in the art to the methods and components of the present invention in view of the disclosure herein. Such modifications are believed to be encompassed in the appended claims.

What is claimed is:

1. A bacterial host cell for the production and secretion of a heterologous protein in high yield comprising:
   (i) a first DNA sequence comprising a gene encoding the heterologous protein operatively linked to a secretory leaderencoding sequence and to an expression control sequence which contains a pL promoter region; and, (ii) a second DNA sequence encoding the C<sub>I</sub>857 Ser-48 repressor depicted in FIG. 1.

2. An improved bacterial host cell of claim 1, wherein the host cell is an enteric bacterium.

3. An improved bacterial host cell of claim 2, wherein the enteric bacterium is *E. coli*.

4. A bacterial host cell according to any of claim 1, wherein the secretory leader-encoding sequence comprises a DNA sequence substantially as depicted in FIG. 3.

5. A bacterial host cell according to claim 1 wherein the heterologous protein is a lymphokine, cytokine, growth hormone, or enzyme.

6. A method for secreting active heterologous protein in high yield from bacterial host cells comprising culturing a cell according to claim 4 under conditions permitting the production and secretion of the heterologous protein.

* * * * *